(12) United States Patent
Nishimoto et al.

(10) Patent No.: US 7,419,819 B2
(45) Date of Patent: Sep. 2, 2008

(54) APPARATUS FOR CELL CULTURE

(75) Inventors: Takahiro Nishimoto, Kakogawa (JP); Yoshiaki Hamada, Hyogo-ken (JP); Seiichi Sakuramoto, Kobe (JP); Keiichi Yokouchi, Hyogo-ken (JP); Akinobu Goto, Kobe (JP); Toshiro Shirakawa, Kobe (JP)

(73) Assignees: Mitsutech Co., Ltd., Hyogo-ken (JP); Gene Medicine Japan Inc., Hyogo-ken (JP)

( * ) Notice: Subject to any disclaimer, the term of this patent is extended or adjusted under 35 U.S.C. 154(b) by 502 days.

(21) Appl. No.: 11/048,559

(22) Filed: Feb. 1, 2005

(65) Prior Publication Data
US 2005/0176138 A1    Aug. 11, 2005

(30) Foreign Application Priority Data
Feb. 9, 2004    (JP) ............................ 2004-032518

(51) Int. Cl.
C12M 1/36    (2006.01)
C12M 1/38    (2006.01)
C12M 3/00    (2006.01)

(52) U.S. Cl. ............... 435/286.4; 435/289.1; 435/303.1

(58) Field of Classification Search ............. 435/286.4, 435/289.1, 303.1; 422/65
See application file for complete search history.

(56) References Cited

U.S. PATENT DOCUMENTS

| | | | |
|---|---|---|---|
| 3,830,701 A | | 8/1974 | Stussman et al. |
| 4,198,483 A | | 4/1980 | Shinohara et al. |
| 4,208,484 A | | 6/1980 | Aihara et al. |
| 4,210,724 A | * | 7/1980 | Sogi et al. ................ 435/309.2 |
| 5,260,872 A | * | 11/1993 | Copeland et al. .............. 435/13 |
| 5,591,627 A | | 1/1997 | Miyamoto et al. |
| 6,309,603 B1 | * | 10/2001 | Locke .......................... 422/72 |
| 6,673,532 B2 | * | 1/2004 | Rao .............................. 435/4 |

(Continued)

FOREIGN PATENT DOCUMENTS

EP    1 270 718    1/2003

(Continued)

OTHER PUBLICATIONS

Cole-Parmer Catalog Apr. 2003 p. 1-3.*

(Continued)

*Primary Examiner*—Walter D. Griffin
*Assistant Examiner*—Shanta G Doe
(74) *Attorney, Agent, or Firm*—Jordan and Hamburg LLP

(57) ABSTRACT

Apparatus for cell culture occupying little space, providing economical efficiency, reducing working labor, faulty manipulation, and promoting the prevention of contamination, which is suitable for small scale cell culture. The apparatus permits the execution of at least a medium replacement process and a passage culture process, and includes an aspirator unit for drawing a liquid, a chemical liquid supply unit for supplying a medium, a liquid for detachment, a washing liquid, a pipetting unit for quantitatively aspirating and discharging the liquid, a centrifugal unit for separating cells from the cell suspension in a centrifuge tube, and a handling unit for moving a culture vessel and the centrifuge tube to each unit. All units being constructed for storage in a clean bench. The apparatus may include a clean bench having a sterile operation space, and the aforementioned units may be removably stored within the sterile operation space.

5 Claims, 7 Drawing Sheets

U.S. PATENT DOCUMENTS

2003/0040104 A1    2/2003    Barbera-Guillem
2003/0054335 A1    3/2003    Taya et al.
2005/0170491 A1*   8/2005    Takagi et al. ............. 435/287.1

FOREIGN PATENT DOCUMENTS

| JP | 7-075549 | 3/1995 |
|---|---|---|
| JP | 8-173140 | 7/1996 |
| JP | 9-098769 | 4/1997 |
| WO | WO/2004/011593 | * 2/2004 |

OTHER PUBLICATIONS

Database WPI Section Ch, Week 200577 Derwent Publications Ltd., London, GB; AN 2004-143834 XP002371358 & WO 2004/011593 T (Japan Sci & Technology Corp) Feb. 5, 2004 abstract.

* cited by examiner

APPARATUS FOR CELL CULTURE

BACKGROUND OF THE INVENTION

1. Field of Invention

The present invention relates to apparatuses for cell culture, and more particularly, relates to an apparatus for cell culture in which automation of small scale cell culture at an experimental level on research is intended.

2. Description of the Related Art

Culture of a cell (particularly, adhesion-dependent cell) generally requires (1) a medium replacement process for replacing an old medium (waste medium) in a culture vessel into a new medium, (2) a passage culture process in which confluent cells in the culture vessel (cells in the state of covering the almost entire bottom face of the culture vessel to form a monolayer) are dispensed into multiple separate culture vessels, and the like.

Specifically, in the aforementioned medium replacement process, a new medium is heated to approximately 37° C.; the waste medium is then drawn with a pipette in a clean bench while appropriately inclining the culture vessel to which the cells are attached; and the aforementioned new medium heated to 37° C. is fed with a pipette into the culture vessel.

Further, in the passage culture process, specifically, the waste medium is removed with a pipette in a clean bench while appropriately inclining the aforementioned culture vessel, followed by washing out calcium ion within the culture vessel as needed. Subsequently, thereto is added trypsin at a predetermined concentration to allow the cells to be detached from the bottom face of the culture vessel, and thereafter, trypsin inhibitor is added to the culture to terminate the aforementioned cell detachment reaction by trypsin. Next, the cell suspension containing trypsin, the trypsin inhibitor and the detached cells are transferred into a centrifuge tube with a pipette, and then, only the cells are sedimented at a rotation frequency of 1000 rpm using a centrifugal separator. Finally, after removing the supernatant containing trypsin and the trypsin inhibitor, a new medium is fed to resuspend the cells, and dispensed into multiple culture vessels.

The medium replacement process and the passage culture process described above required for cell culture have been conventionally carried out, generally according to manual procedures, which must be conducted carefully while paying attention to prevent contamination with bacteria and the like. Accordingly, enormous time and labor have been required.

On the other hand, apparatuses for cell culture in which automation of the cell culture is intended have been developed in these days. For example, such apparatuses are disclosed in JP-A Nos. H7-75549, H8-173140, H9-98769 and the like.

In accordance with summary of the conventional automated apparatus for cell culture described above, a cell culture bath, a circulatory system for supplying a medium into the cell culture bath and an accessory for supplementing a culture fluid or a culture gas to the medium are provided, with the apparatus being comparatively extensive, requiring a great cost for equipment, and being designed for the principal purpose of large scale culture of cells. Therefore, it is difficult to apply the conventional automated apparatus for cell culture as described above to the small scale cell culture at an experimental level on research.

SUMMARY OF THE INVENTION

The present invention was made taking into account of these problems, and an object of the present invention is to provide an apparatus for cell culture exhibiting favorable property to occupy little space and economical efficiency, capable of reducing the working labor, faulty manipulation and the like, and of promoting the prevention of contamination, which is suitable for small scale cell culture at an experimental level on research, in particular.

The present invention which was made to solve the aforementioned problem is an apparatus for cell culture in which at least a medium replacement process and a passage culture process can be executed, which comprises (a) an aspirator unit for drawing a liquid, (b) a chemical liquid supply unit for supplying a medium, a liquid for detachment, a washing liquid and the like, (c) a pipetting unit for quantitatively aspirating and discharging the liquid, (d) a centrifugal unit for separating cells from the cell suspension in a centrifuge tube, and (e) a handling unit for carrying a culture vessel and the centrifuge tube to each unit, wherein all units are constructed such that they can be stored in a clean bench. Moreover, the present invention is an apparatus for cell culture which further comprises (f) a clean bench having a sterile operation space, wherein the aforementioned units are stored within the sterile operation space in a removable manner.

Because the apparatus for cell culture includes an aspirator unit, a chemical liquid supply unit, a pipetting unit, a centrifugal unit and a handling unit, (1) a medium replacement process for replacing the waste medium in a culture vessel into a new medium; (2) a passage culture process in which confluent cells in the culture vessel are dispensed into multiple separate culture vessels, and the like can be automatically executed. In addition, the apparatus for cell culture is constructed such that all units can be stored in a clean bench which has been generally used for cell culture, therefore, the cost for equipment can be reduced, resulting in suitability for small scale cell culture at an experimental level on research. Furthermore, automation is intended by way of each component unit according to the apparatus for cell culture, therefore, working labor, faulty manipulation and the like in the passage culture process and the like can be reduced, and additionally, prevention of contamination can be promoted. In addition, because the component units are stored within a sterile operation space of a clean bench in a removable manner according to the apparatus for cell culture, maintenance such as washing after use, sterilizing treatment, inspection and the like can be facilitated.

The handling unit described above may comprise (g) a slide module having a culture vessel table and a centrifuge tube table for mounting the culture vessel and the centrifuge tube, respectively, and being constructed such that the culture vessel table and the centrifuge tube table are movable to each operation position of the aspirator unit, chemical liquid supply unit and pipetting unit, and (h) a carrying module which is constructed such that it can hold the culture vessel and the centrifuge tube and that they can be carried to a predetermined position of the culture vessel table and the centrifuge tube table, respectively, of the slide module.

According to this handling unit, accuracy of handling and variance of carrying of the culture vessel and the like can be improved, and the continuous processing of multiple culture vessels is enabled through separately being equipped the aspirator unit that relates to receiving and supplying the liquid, the slide module that moves the culture vessel to the chemical liquid supply unit and pipetting unit, and the carrying module that carries the culture vessel and the like to this slide module and the like.

The aforementioned culture vessel table may be constructed in a shakable manner. By thus constructing the culture vessel table in a shakable manner, the culture vessel table can be shaken, for example, after supplying a liquid for detachment or the like, thereby capable of spreading the liquid for detachment or the like all over the bottom of the culture vessel. Consequently, uniformity of the effect of detachment and the like can be improved.

The apparatus for cell culture may further include a detachment promotion unit for keeping the mounted culture vessel at a temperature of approximately 36 to 37° C. By providing such a detachment promotion unit, the temperature of the culture vessel can be kept in a suitable range after supplying the liquid for detachment, thereby enabling the promotion of detachment of the cells. As a result, reduction of the operation time period for the passage culture process can be further promoted.

Moreover, the apparatus for cell culture may have a centrifuge tube cap opening and closing unit which is constructed such that it holds the cap of the centrifuge tube, and can rotates. By providing such a centrifuge tube cap opening and closing unit, opening and closing of the cap of the centrifuge tube is enabled within the sterile operation space of the clean bench, and thus, prevention of contamination can be promoted.

As explained hereinabove, the apparatus for cell culture of the present invention is extremely downsized, exhibits excellent economical efficiency and facility in installation, and promotes the reduction in working labor, faulty manipulation and the like as well as the prevention of contamination. Accordingly, it is suitably used for small scale cell culture at particularly an experimental level on research.

DESCRIPTION OF THE PREFERRED EMBODIMENTS

Figure 1:
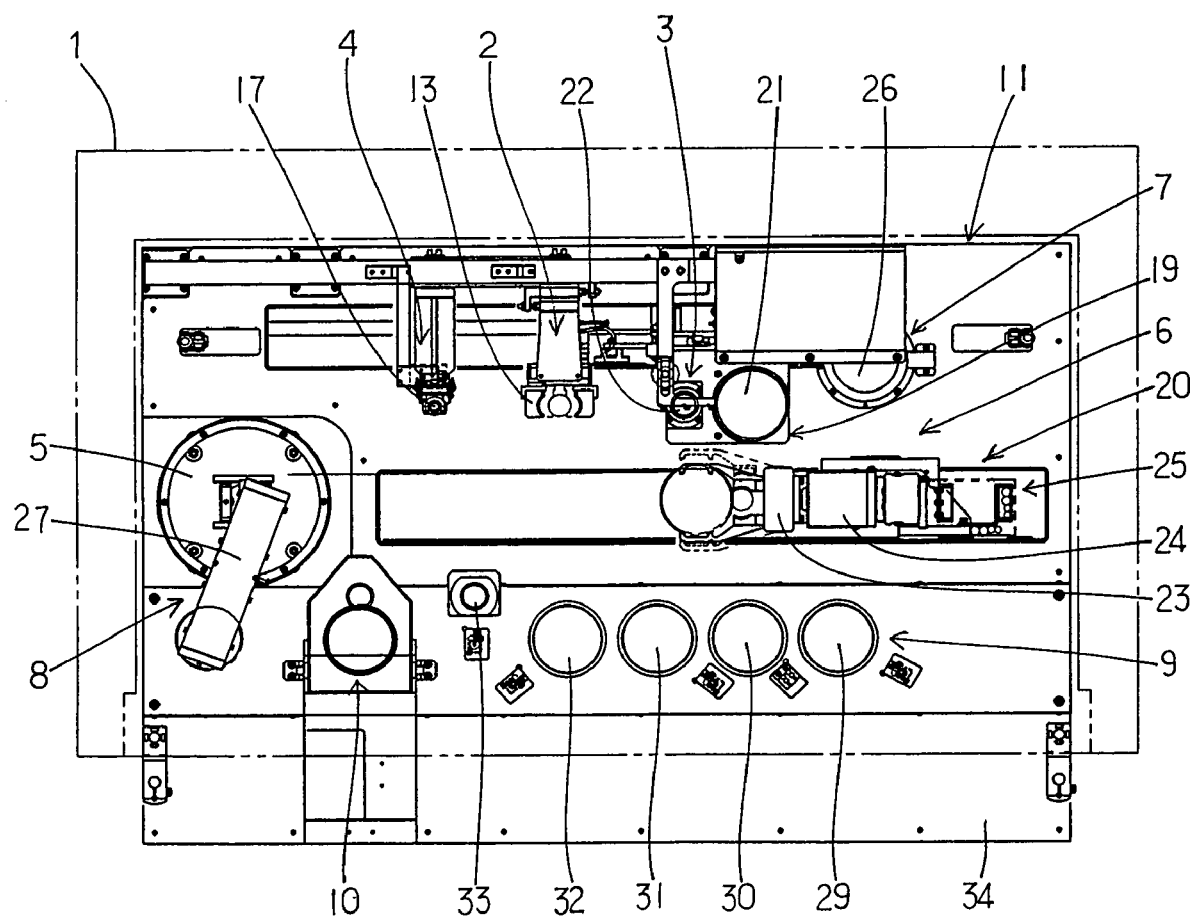
FIG. 1 is a plan view illustrating an apparatus for cell culture according to one embodiment of the present invention showing partially different cross sections.
Figure 2:
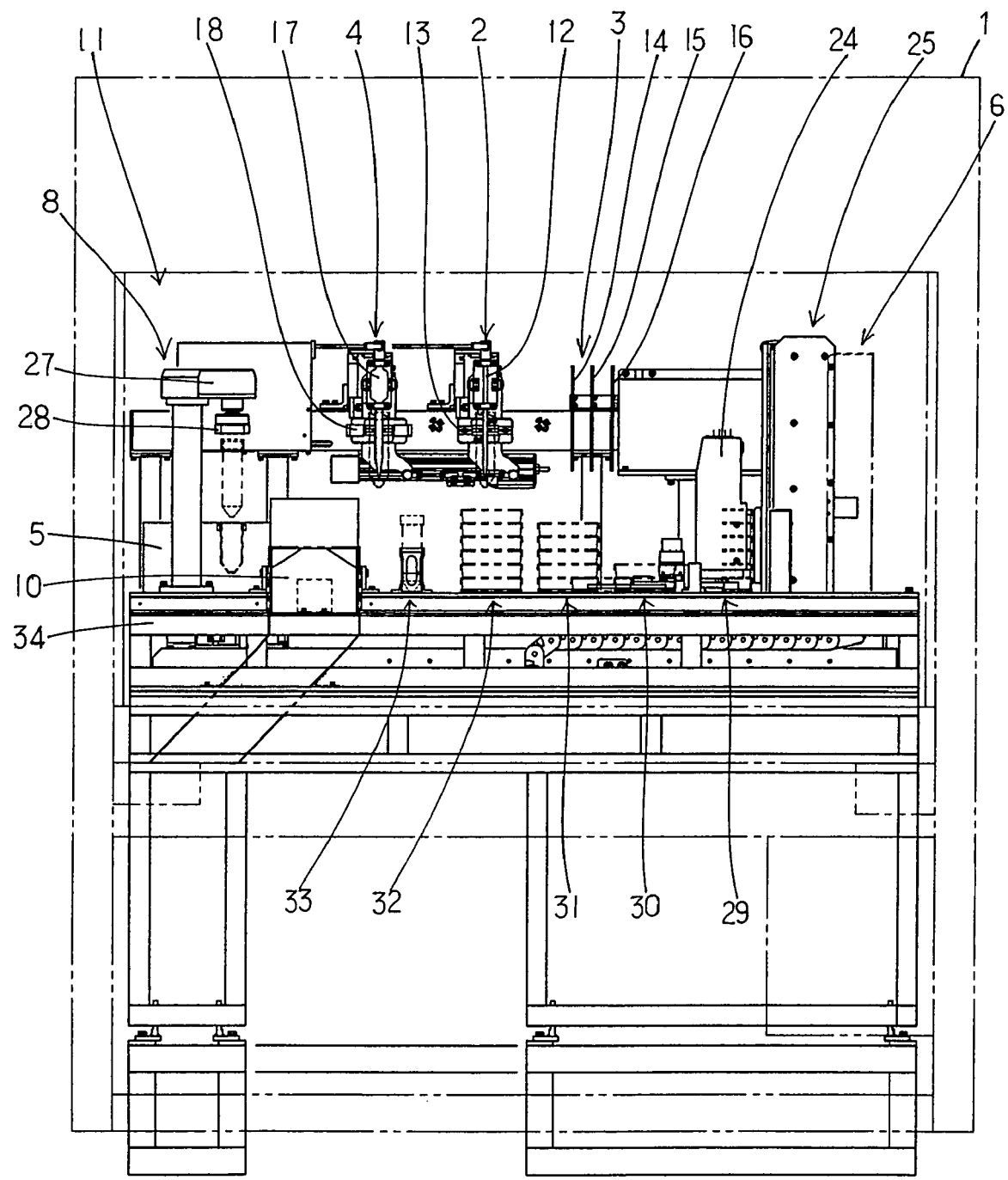
FIG. 2 is a front view illustrating the apparatus for cell culture shown in FIG. 1.
Figure 3:
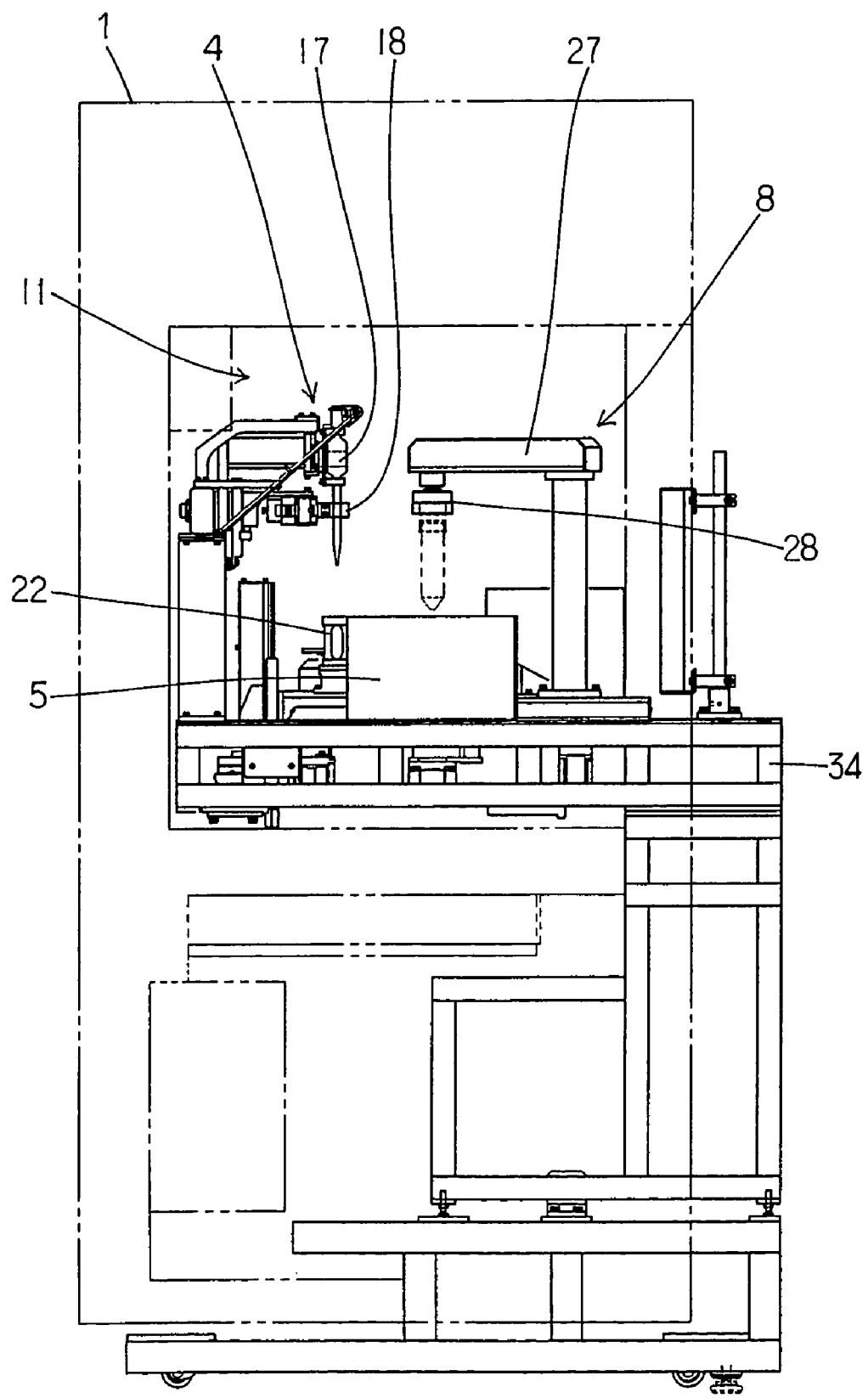
FIG. 3 is a left side view illustrating the apparatus for cell culture shown in FIG. 1.

The apparatus for cell culture shown in FIG. 1 to FIG. 3 has a clean bench 1, and each unit stored within this clean bench 1. The apparatus for cell culture includes, as the each unit, an aspirator unit 2, a chemical liquid supply unit 3, a pipetting unit 4, a centrifugal unit 5, a handling unit 6, detachment promotion unit 7, a centrifuge tube cap opening and closing unit 8, vessel supply and elimination unit 9 and used vessel elimination unit 10.

The clean bench 1 has a sterile operation space 11 with an opening at the front, which is similar to those generally used in experimental researches. This clean bench 1, specifically, has a sterilization lamp in the sterile operation space 11, and may be of a blow-out type in which sterile air blows out from above or from back, a biological hazard corresponding type in which sterile air flows to make an air curtain, or the like.

The aspirator unit 2 draws the liquid in the culture vessel and the centrifuge tube, and discards them outside, which is provided in the central area in the back of the sterile operation space 11 of the clean bench 1. This aspirator unit 2, specifically, includes a pipette 12 perpendicularly provided with its tip being directed downward, a centrifuge tube holding part 13 that holds the centrifuge tube with this pipette 12 inserted, a pipe connected to the rear end of the pipette 12, a suction pump connected to this pipe, and the like. This centrifuge tube holding part 13 is constructed in a manner which can relatively rotate the centrifuge tube at a predetermined angle with respect to the pipette 12, and thus, the tip of the pipette 12 can abut on the inner wall of the centrifuge tube. Further, the pipette 12 and the centrifuge tube holding part 13 are constructed such that they can be synchronously rotated, thereby facilitating drawing of the liquid in the centrifuge tube.

The chemical liquid supply unit 3 supplies the medium, the liquid for detachment, the washing liquid and the like into the culture vessel and the centrifuge tube, and is provided in the central area in the back of the sterile operation space 11. This chemical liquid supply unit 3, specifically, has a medium supply module, a liquid for detachment supply module and a washing liquid supply module. This medium is a matrix for use in culture of cells, and may contain nutrients such as amino acid, vitamin, glucose and the like, and proliferation factors such as calf serum, and the like. The liquid for detachment forms a suspension of single cells after stripping the adhesion between the cells as well as the cell and the vessel wall, and specifically, trypsin/EDTA (PET) or the like may be used. The washing liquid washes cells before charging the liquid for detachment upon formation of the suspension of the single cells, and specifically, PBS (−) or the like may be used.

The medium supply module, specifically, includes a supply nozzle 14 perpendicularly provided with its tip being directed downward, a supply tube connected to the rear end of the supply nozzle 14, a pump connected to the supply tube, a reservoir tank for storing a medium to be supplied, and the like. This reservoir tank may have a function to store the medium at a low temperature, and be able to keep it at a predetermined temperature of approximately 36° C. prior to the supply. Also, when the reservoir tank is provided outside of the clean bench 1, a filter may be provided in the supply route, thereby promoting reduction of contamination. On the other hand, when the reservoir tank is provided inside of the clean bench 1, performances for replacing the medium may be considered upon laying out.

The liquid for detachment supply module has a structure which is similar to the medium supply module as described above, and specifically, it includes a supply nozzle 15 perpendicularly provided with its tip being directed downward, a supply tube connected to the rear end of the supply nozzle 15, a pump connected to the supply tube, a reservoir tank for storing a liquid for detachment to be supplied, and the like.

The washing liquid supply module also has a structure which is similar to the medium supply module as described above, and specifically, it has a supply nozzle 16 perpendicularly provided with its tip being directed downward, a supply tube connected to the rear end of the supply nozzle 16, a pump connected to the supply tube, a reservoir tank for storing a washing liquid to be supplied, and the like.

The pipetting unit 4 quantitatively aspirates and discharges the liquid in the culture vessel and centrifuge tube, and is provided in the back of the sterile operation space 11. This pipetting unit 4, specifically, has a Komagome pipette 17 perpendicularly provided with its tip being directed downward, a centrifuge tube holding part 18 that holds the centrifuge tube with this Komagome pipette 17 inserted, a pipe connected to the rear end of the Komagome pipette 17, a pump connected to this pipe, and the like. This centrifuge tube holding part 18 is also constructed in a manner which can relatively rotate the centrifuge tube at a predetermined angle with respect to the Komagome pipette 17, such that the tip of the Komagome pipette 17 can abut on the inner wall of the centrifuge tube, similarly to the centrifuge tube holding part 13 of the aspirator unit 2. Further, the Komagome pipette 17 and the centrifuge tube holding part 18 are also constructed such that they can be synchronously rotated similarly to the aspirator unit 2, thereby facilitating drawing of the liquid in the centrifuge tube.

The Komagome pipette 17 in the pipetting unit 4, the pipette 12 in the aspirator unit 2, the supply nozzles 14, 15 and 16 in the chemical liquid supply unit 3 are disposed in a line in a horizontal direction.

The centrifugal unit 5 centrifuges cells from the cell suspension within the centrifuge tube, and is provided left side in the sterile operation space 11. This centrifugal unit 5 is not particularly limited, but any known centrifugal separation means may be employed. Specific structure of this centrifugal unit 5 may be e.g., a structure in which a centrifuge tube received substantially vertically at an eccentric position is rotated using a servo motor, thereby inclining the bottom of the centrifuge tube to the horizontal direction by the centrifugal force. For the purpose of securing smooth rotation, a counter weight may be provided.

The handling unit 6 carries the culture vessel and the centrifuge tube to each unit, and is provided in the central area in the sterile operation space 11. This handling unit 6, specifically, has a slide module 19 and a carrying module 20.

The slide module 19 has a culture vessel table 21 on which the culture vessel is mounted, a centrifuge tube table 22 on which the centrifuge tube is mounted lengthwise, and a slide mechanism which allows the culture vessel table 21 and the centrifuge tube table 22 to move the horizontal direction and the up and down direction. The culture vessel table 21 and the centrifuge tube table 22 are provided down below the pipetting unit 4, the aspirator unit 2 and the chemical liquid supply unit 3. Such a slide module 19 is constructed so that the culture vessel and the centrifuge tube mounted on the culture vessel table 21 and centrifuge tube table 22, respectively, are movable to each working position of the aspirator unit 2, the chemical liquid supply unit 3 and the pipetting unit 4. Further, the culture vessel table 21 has a function to incline and a function to shake. Such an inclining function facilitates pipetting from the culture vessel and the like, and the shaking function enables spreading the charged chemical liquid all over the bottom of the culture vessel. As specific mode of movement in this shaking function, a mode of movement resulting from precessionally rotating central vertical axis of the culture vessel table 21 is preferred. Means for achieving the construction and function of the slide module 19 as described above is not particularly limited, but any known means may be employed.

The carrying module 20 has a holding part 23 constructed in a manner capable of holding the culture vessel and the centrifuge tube, a deviation part 24 constructed to enable the holding part 23 to swing, a displacement part 25 constructed to enable the holding part 23 to be slidable in the horizontal direction and the up and down direction, a driving motor and the like. This carrying module 20 is constructed such that the culture vessel and the centrifuge tube can be held by the holding part 23, and that the culture vessel and the centrifuge tube can be carried to a predetermined position such as a vessel supply and elimination unit 9 (described below), the culture vessel table 21 and centrifuge tube table 22, the centrifugal unit 5, the pipetting unit 4, the aspirator unit 2, the detachment promotion unit 7, the centrifuge tube cap opening and closing unit 8, the used vessel elimination unit 10 and the like by the deviation part 24 and displacement part 25. Means for achieving the construction and function of the carrying module 20 as described above is not particularly limited, but any known means may be employed.

The detachment promotion unit 7 has a flat heater 26, a control mechanism and the like, and keeps the disposed culture vessel at a temperature of approximately 36 to 37° C. Through disposing a culture vessel having a liquid for detachment charged therein on the flat heater 26 of this detachment promotion unit 7, heating at approximately 36° C., and incubating for a predetermined period of time, cells in the culture vessel are detached, thereby achieving the released stated in a shorter period of time.

The centrifuge tube cap opening and closing unit 8 has a reverse L-shaped stand 27, a zip part 28 perpendicularly provided on the bottom face of the tip portion of this stand 27, a driving motor and the like. This centrifuge tube cap opening and closing unit 8 is constructed such that the cap of the centrifuge tube is held by the zip part 28, and that the zip part 28 can be rotated by the driving motor or the like. As a result, opening and closing of the cap of the centrifuge tube can be perfected.

The vessel supply and elimination unit 9 is a part for conducting the supply and elimination of the culture vessel and the centrifuge tube, and is provided at the front in the sterile operation space 11. This vessel supply and elimination unit 9, specifically, has a culture vessel storage part 29 for storing multiple sterile culture vessels for use in the passage culture, a passage culture vessel placing part 30 for placing the culture vessel subjected to the passage culture, a culture vessel ejecting part 31 for disposing multiple culture vessels after completing the operation, a medium replacement vessel placing part 32 for placing multiple culture vessels subjected to replacement of the medium, a centrifuge tube storage part 33 for storing sterile centrifuge tube for use in the passage culture, and the like. Supply and elimination of the culture vessels and centrifuge tubes to and from the vessel supply and elimination unit 9 may be manually performed by the operator. Examples of this culture vessel include e.g., dishes, flasks, plates and the like.

The used vessel elimination unit 10 eliminates the used culture vessel and centrifuge tube outside. The used vessel elimination unit 10 is not particularly limited as long as elimination of the culture vessel and the like is enabled, but any of various known means may be employed. However, the unit preferably includes, for example, a conveyer for eliminating used culture vessels and the like, a receiving vessel filled with a liquid for sterilization such as hypochlorous acid, and the like.

The aspirator unit 2, the chemical liquid supply unit 3, the pipetting unit 4, the centrifugal unit 5, the handling unit 6, the detachment promotion unit 7, the centrifuge tube cap opening and closing unit 8, the vessel supply and elimination unit 9 and the used vessel elimination unit 10 constructing the operation part of the apparatus for cell culture are installed on a bogie 34 having a substantially angular U shaped cross section as shown in FIG. 3, and stored in the sterile operation space 11 of the clean bench 1 in a removable manner. Thus, in the apparatus for cell culture, each unit can be taken out from the sterile operation space 11 through drawing the bogie 34 from the clean bench 1, and thus, washing treatment, sterilization treatment, and maintenance such as inspection and repair of each unit can be performed easily and certainly.

To the apparatus for cell culture may be added a dust attraction function at a site where dust may be generated in the sterile operation space 11 of the clean bench 1. Accordingly, cleanliness in the sterile operation space 11 of the clean bench 1 can be improved, and prevention of contamination can be promoted.

Preferred examples of the material of each component part of the apparatus for cell culture include stainless, hard alumite treatment materials of aluminum alloy, and the like. Although sterilization of the sterile operation space 11 of the clean bench 1 is conducted by lighting a sterilization lamp in the apparatus for cell culture while it is not used, use of such a material may improve the durability.

According to the apparatus for cell culture, (1) a medium replacement process in which the waste medium in the culture vessel is replaced with a new medium, (2) a passage culture process in which confluent cells in the culture vessel are dispensed into multiple separate culture vessels, and the like can be automatically executed by cooperative operation of each unit. Moreover, because all units in the present apparatus for cell culture are constructed in a manner which can be stored in a sterile operation space 11 of the clean bench 1 which has been generally used for cell culture, the cost for equipment can be reduced, resulting in suitability for small scale cell culture at an experimental level on research. Furthermore, automation is intended by each component unit according to the apparatus for cell culture, therefore, working labor, faulty manipulation and the like in the passage culture process and the like can be reduced, in addition thereto, prevention of contamination can be promoted. Moreover, because the apparatus for cell culture has component units stored in the sterile operation space of the clean bench in a removable manner, washing and sterilization treatment after use as well as maintenance such as inspection may be facilitated.

Figure 4:
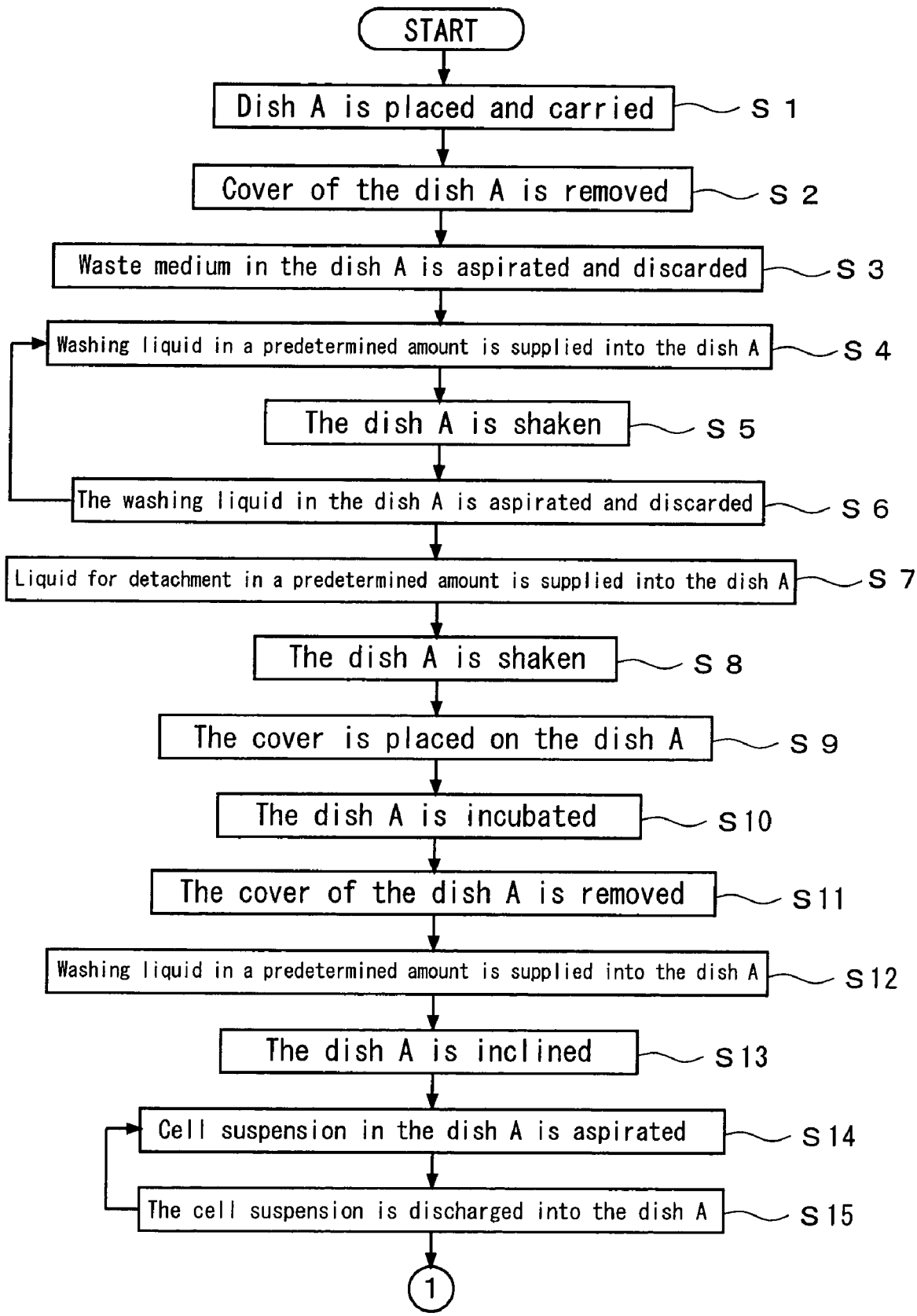
FIG. 4 is a first flow chart illustrating a passage culture process in which the apparatus for cell culture shown in FIG. 1 is used.
Figure 5:
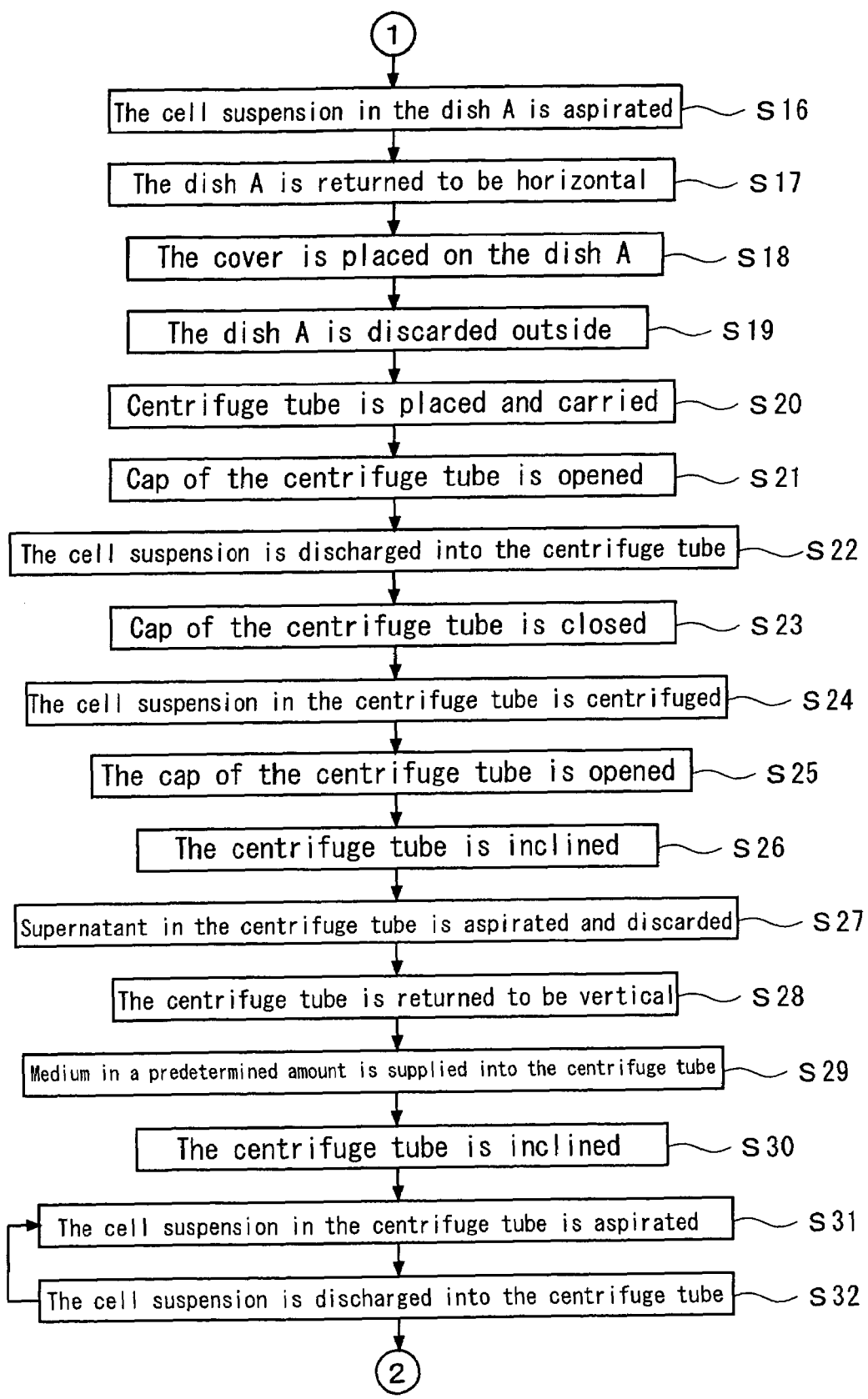
FIG. 5 is a second flow chart illustrating a passage culture process in which the apparatus for cell culture shown in FIG. 1 is used.
Figure 6:
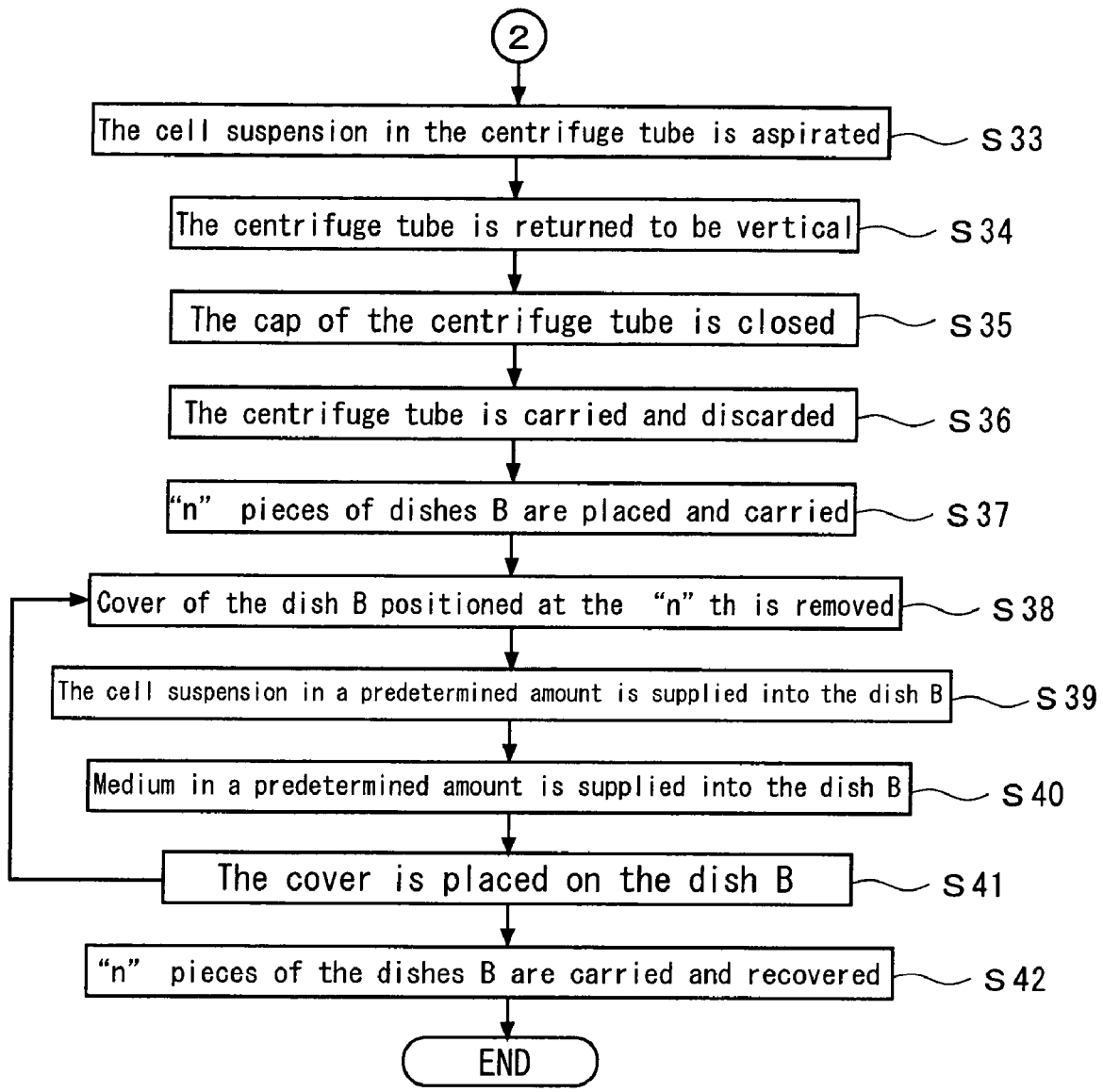
FIG. 6 is a third flow chart illustrating a passage culture process in which the apparatus for cell culture shown in FIG. 1 is used.

The passage culture process in which the apparatus for cell culture is used is explained below with reference to the flow charts shown in FIG. 4 to FIG. 6. First, a dish A filled with cells for passage culture which is placed in a passage culture vessel placing part 30 is carried on the culture vessel table 21 of the slide module 19 by the carrying module 20 (S1), then, the cover of the dish A is held up and removed by the carrying module 20 (S2). Next, the dish A is moved to the aspirator unit 2 by the slide module 19, and the waste medium is aspirated to discard (S3). Next, the dish A is moved to the washing liquid supply module by the slide module 19, and the washing liquid in a predetermined amount is supplied into the dish A by the washing liquid supply module (S4). The culture vessel table 21 is shaken to allow the washing liquid to spread all over the bottom of the culture vessel (S5), and thereafter, it is moved to the aspirator unit by the slide module 19 to aspirate and discard the washing liquid in the dish A by the aspirator unit 2 (S6). The operations of S4 to S6 are repeated predetermined times.

Next, the dish A is moved to the liquid for detachment supply module by the slide module 19, and the liquid for detachment in a predetermined amount is supplied to the dish A by the liquid for detachment supply module (S7). The culture vessel table 21 is then shaken to spread the liquid for detachment all over the bottom (S8). Thereafter, the cover is placed on the dish by the carrying module 20 (S9), and the dish A is carried on the flat heater 26 of the detachment promotion unit 7. The dish A is kept at a predetermined temperature of approximately 36° C. for a predetermined time period to accelerate the detachment of the cells (S10).

Thereafter, the dish A is carried on the culture vessel table 21 by the carrying module 20, and the cover is held up and removed by the carrying module 20 (S11). Next, the dish A is moved to the washing liquid supply module by the slide module 19, and the washing liquid in a predetermined amount is supplied into the dish A by the washing liquid supply module (S12). The culture vessel table 21 is inclined (S13), and the dish A is moved to the pipetting unit 4 by the slide module 19. Next, the cell suspension in the dish A is aspirated by the pipetting unit 4 (S14), and discharged into the dish A (S15) The pipetting of S14 and S15 is repeated predetermined times, and the cell suspension is stirred. Finally, the cell suspension is aspirated into the Komagome pipette 17 of the pipetting unit 4 (S16).

Next, the culture vessel table 21 returned to be horizontal (S17), and the cover is placed by the carrying module 20 (Sl8). The dish A is then carried to the used vessel elimination unit 10 by the carrying module 20 similarly, and discarded outside (S19). Thereafter, the centrifuge tube stored in the centrifuge tube storage part 33 is held by the carrying module 20 (S20), and carried to the centrifuge tube cap opening and closing unit 8. The cap of the centrifuge tube is opened by the centrifuge tube cap opening and closing unit 8 (S21). The uncapped centrifuge tube is carried to the pipetting unit 4 by the handling unit 6, and the cell suspension is discharged into the centrifuge tube by the pipetting unit 4 (S22). The centrifuge tube into which the cell suspension was discharged is carried to the centrifuge tube cap opening and closing unit 8 by the handling unit 6, and the cap of the centrifuge tube is closed by the centrifuge tube cap opening and closing unit 8 (S23). This centrifuge tube is carried to the centrifugal unit 5 by the carrying module 20, and centrifugal separation is conducted with the centrifugal unit at a predetermined rotational frequency for a predetermined time period (S24) to separate cells from the cell suspension by precipitation.

After the centrifugal separation, the centrifuge tube is carried to the centrifuge tube cap opening and closing unit 8 by the carrying module 20, and the cap of the centrifuge tube is opened by the centrifuge tube cap opening and closing unit 8 (S25). The centrifuge tube is moved to the aspirator unit 2 by the handling unit 6. Next, while inclining the centrifuge tube at a predetermined angle by the aspirator unit 2 (S26), supernatant in the centrifuge tube is aspirated and discarded (S27). Thereafter, the centrifuge tube is returned to be vertical by the aspirator unit 2 (S28), and the centrifuge tube is moved to the medium supply module by the slide module 19, followed by supplying a medium in a predetermined amount into the centrifuge tube by the medium supply module (S29).

Thereafter, the centrifuge tube is moved to the pipetting unit 4 by the slide module 19, and the centrifuge tube is inclined at a predetermined angle by the pipetting unit 4 (S30) In this state, the cell suspension in the centrifuge tube is aspirated by the pipetting unit 4 (S31), and is discharged into the centrifuge tube (S32). The pipetting of S31 and S32 is repeated predetermined times, and the cell suspension is stirred. Finally, the cell suspension is aspirated into the Komagome pipette 17 of the pipetting unit 4 (S33).

Next, the centrifuge tube is returned to be vertical by the pipetting unit 4 (S34), and the centrifuge tube is carried to the centrifuge tube cap opening and closing unit 8 by the handling unit 6. Then the cap of the centrifuge tube is closed by the centrifuge tube cap opening and closing unit 8 (S35), and the centrifuge tube is carried to the used vessel elimination unit 10 by the carrying module 20, and is discarded outside (S36).

On the other hand, multiple number (n pieces) of sterilized dishes B which had been stored in the culture vessel storage part 29 are carried all at once on the culture vessel table 21 through holding the undermost dish B by the carrying module 20 as they are in the state of being stacked (S37). Next, the cover of the dish B positioned at the "n"th from the bottom is held up by the carrying module 20 to remove (S38), and the cell suspension in a predetermined amount is supplied into the dish B at the "n"th position by the pipetting unit 4 (S39). Then, a medium in a predetermined amount is supplied into the dish B at the "n"th position by the medium supply module (S40), and the cover is placed on the dish B at the "n"th position by the carrying module 20 (S41). The operations of S38 to S41 are repeated sequentially from the upper dish B to the lower dish B, and finally, n pieces of the dishes B are carried all at once by the carrying module 20 to the culture vessel ejecting part 31 as they are in the state of being stacked to complete the passage culture process (S42). The dishes B in the culture vessel ejecting part 31 are carried into an incubator by the operator.

Figure 7:
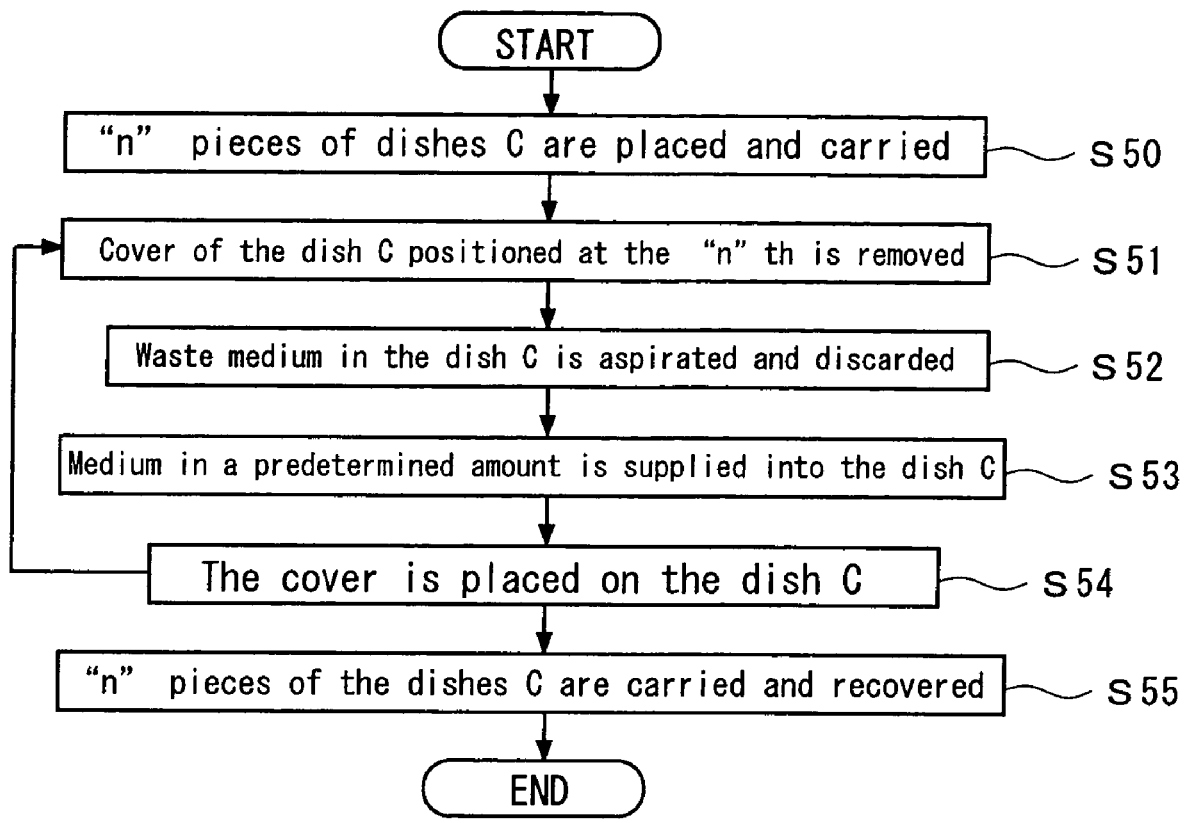
FIG. 7 is a flow chart illustrating a medium replacement process in which the apparatus for cell culture shown in FIG. 1 is used.

The medium replacement process in which the apparatus for cell culture is used is explained below with reference to the flow chart shown in FIG. 7. First, multiple pieces (n pieces) of the cells-charged dishes C for medium replacement which are placed in the medium replacement vessel placing part 32 are carried on the culture vessel table 21 all at once by the carrying module 20 through holding the undermost dish C as they are in the state of being stacked (S50). Next, the cover of the dish C positioned at the "n"th is held up by the carrying module 20 to remove (S51), and the waste medium in the dish C positioned at the "n"th is aspirated by the aspirator unit 2 to discard (S52). Then, a medium in a predetermined amount is supplied into the dish C at the "n"th position by the medium supply module (S53), and the cover is placed on the dish C at the "n"th position by the carrying module 20 (S54). The operations of S51 to S54 are repeated sequentially from the upper dish C to the lower dish C, and finally, n pieces of the dishes C are carried all at once by the carrying module 20 to the culture vessel ejecting part 31 as they are in the state of being stacked to complete the medium replacement process (S55). The dishes C in the culture vessel ejecting part 31 are carried into an incubator by the operator.

The apparatus for cell culture of the present invention is not anyhow limited to the embodiment as described above, but a mode in which a clean bench 1 is not provided is also permitted, and any mode that allows other operation to be executed in addition to the passage culture process and the medium replacement process is also permitted.

What is claimed is:

1. An apparatus for cell culture wherein at least a medium replacement process and a passage culture process can be executed, said apparatus comprising:
    an aspirator unit for drawing a liquid,
    a chemical liquid supply unit for supplying a medium, a liquid for detachment, or a washing liquid,
    a pipetting unit for quantitatively aspirating and discharging the liquid,
    a centrifugal unit for separating cells from a cell suspension in a centrifuge tube,
    a handling unit for carrying a culture vessel and the centrifuge tube to said aspirator unit, chemical liquid supply unit, pipetting unit, and centrifugal unit, and
    a clean bench having a sterile operation space in which said aspirator unit, chemical liquid supply unit, pipetting unit, centrifugal unit and handling unit are removably stored within the sterile operation space, wherein
    said handling unit comprises:
        a slide module having a culture vessel table and a centrifuge tube table for mounting the culture vessel and the centrifuge tube, respectively, and being constructed such that the culture vessel table and the centrifuge tube table are movable to each operation position of the aspirator unit, chemical liquid supply unit and pipetting unit, and
        a carrying module which is constructed such that the carrying module can hold the culture vessel and the centrifuge tube, and that the culture vessel and the centrifuge tube can be carried to a predetermined position of the culture vessel table and the centrifuge tube table, respectively, of the slide module,
        said carrying module having a holding part constructed in a manner capable of holding the culture vessel and the centrifuge tube, a deviation part constructed to enable the holding part to swing, and a displacement part constructed to enable the holding part to be slidable in a horizontal direction and an up an down direction.

2. The apparatus for cell culture according to claim 1 wherein said culture vessel table is constructed to be shakable.

3. The apparatus for cell culture according to claim 1 further comprising a detachment promotion unit for keeping the culture vessel at a temperature of approximately 36 to 37° C.

4. The apparatus for cell culture according to claim 1 further comprising a centrifuge tube cap opening and closing unit which is constructed such that it holds the cap of the centrifuge tube, and can rotate the cap.

5. An apparatus for cell culture wherein at least a medium replacement process and a passage culture process can be executed, said apparatus comprising:
    an aspirator unit for drawing a liquid,
    a chemical liquid supply unit for supplying a medium, a liquid for detachment, or a washing liquid,
    a pipetting unit for quantitatively aspirating and discharging the liquid,
    a centrifugal unit for separating cells from a cell suspension in a centrifuge tube, and
    a handling unit for carrying a culture vessel and the centrifuge tube to said aspirator unit, chemical liquid supply unit, pipetting unit, and centrifugal unit, wherein
    said aspirator unit, chemical liquid supply unit, pipetting unit, centrifugal unit and handling unit are constructed such that they can be placed in a clean bench, and
    said handling unit comprises:
        a slide module having a culture vessel table and a centrifuge tube table for mounting the culture vessel and the centrifuge tube, respectively, and being constructed such that the culture vessel table and the centrifuge tube table are movable to each operation position of the aspirator unit, chemical liquid supply unit and pipetting unit, and
        a carrying module which is constructed such that the carrying module can hold the culture vessel and the centrifuge tube, and that the culture vessel and the centrifuge tube can be carried to a predetermined position of the culture vessel table and the centrifuge tube table, respectively, of the slide module.

* * * * *